(12) United States Patent
L'Alloret et al.

(10) Patent No.: US 6,998,426 B2
(45) Date of Patent: Feb. 14, 2006

(54) NANOEMULSION CONTAINING NONIONIC POLYMERS, AND ITS USES

(75) Inventors: Florence L'Alloret, Paris (FR); Odile Aubrun-Sonneville, Antony (FR); Jean-Thierry Simonnet, Paris (FR)

(73) Assignee: L'Oreal, Paris (FR)

( * ) Notice: Subject to any disclaimer, the term of this patent is extended or adjusted under 35 U.S.C. 154(b) by 233 days.

(21) Appl. No.: 09/903,768

(22) Filed: Jul. 13, 2001

(65) Prior Publication Data

US 2002/0035182 A1 Mar. 21, 2002

(30) Foreign Application Priority Data

Jul. 13, 2000 (FR) .................................. 00 09222

(51) Int. Cl.
*A61K 31/74* (2006.01)
*A61K 9/107* (2006.01)

(52) U.S. Cl. ........................ 523/102; 523/105; 524/35; 524/306; 524/312; 524/321; 524/800; 524/803; 524/804; 424/78.03; 424/78.04; 424/400; 424/485; 424/486

(58) Field of Classification Search ................. 524/35, 524/306, 312, 321, 800, 803, 804; 523/102, 523/105; 424/78.03, 78.04, 400, 485, 486
See application file for complete search history.

(56) References Cited

U.S. PATENT DOCUMENTS

| | | | | |
|---|---|---|---|---|
| 3,301,829 | A | * | 1/1967 | Woodward et al. ......... 526/271 |
| 3,390,010 | A | * | 6/1968 | Frerker et al. ............. 427/389 |
| 4,137,180 | A | | 1/1979 | Naik et al. |
| 4,874,554 | A | | 10/1989 | Lange et al. |
| 5,364,633 | A | | 11/1994 | Hill et al. |
| 5,411,744 | A | | 5/1995 | Hill et al. |
| 5,591,449 | A | * | 1/1997 | Bollens et al. ............. 424/450 |
| 5,599,524 | A | * | 2/1997 | Morawsky et al. ........... 424/47 |
| 5,753,241 | A | | 5/1998 | Ribier et al. |
| 5,925,341 | A | * | 7/1999 | Cervantes et al. ....... 424/78.03 |
| 6,004,566 | A | * | 12/1999 | Friedman et al. ........... 424/400 |
| 6,120,778 | A | | 9/2000 | Simonnet |
| 6,274,150 | B1 | | 8/2001 | Simonnet et al. |
| 6,287,377 | B1 | * | 9/2001 | Binns et al. ................ 106/499 |
| 6,335,022 | B1 | | 1/2002 | Simonnet et al. |
| 6,375,960 | B1 | | 4/2002 | Simonnet et al. |
| 6,413,527 | B1 | | 7/2002 | Simonnet et al. |
| 6,419,946 | B1 | | 7/2002 | Sonneville et al. |
| 6,432,439 | B1 | * | 8/2002 | Suzuki et al. .............. 424/427 |
| 6,440,431 | B1 | * | 8/2002 | Yoshida et al. ............ 424/401 |
| 6,461,625 | B1 | | 10/2002 | Simonnet et al. |
| 6,464,990 | B1 | | 10/2002 | Simonnet et al. |
| 6,569,414 | B1 | * | 5/2003 | Bernecker et al. ....... 424/70.15 |
| 2002/0012645 | A1 | * | 1/2002 | Midha et al. .............. 424/70.2 |
| 2003/0138465 | A9 | * | 7/2003 | Douin et al. ................ 424/401 |

FOREIGN PATENT DOCUMENTS

| | | |
|---|---|---|
| DE | 196 41 672 A1 | 4/1998 |
| DE | 198 16 662 A1 | 10/1999 |
| EP | 0 107 199 A2 | 5/1984 |
| EP | 0 696 452 A1 | 2/1996 |
| EP | 0 728 460 A1 | 8/1996 |
| EP | 0 780 114 A1 | 6/1997 |
| EP | 0 968 704 A1 | 1/2000 |
| FR | 2 787 026 | 6/2000 |
| FR | 2 787 027 | 6/2000 |
| FR | 2 787 325 | 6/2000 |
| FR | 2 787 703 | 6/2000 |
| FR | 2 787 728 | 6/2000 |
| GB | 131820 | 9/1919 |
| WO | WO 94/00508 | 1/1994 |
| WO | WO 00/61083 | 10/2000 |

* cited by examiner

*Primary Examiner*—Tae H. Yoon
(74) *Attorney, Agent, or Firm*—Oblon, Spivak, McClelland, Maier & Neustadt, P.C.

(57) ABSTRACT

These objects and others may be accomplished with the present invention, the first embodiment of which provides an oil-in-water nanoemulsion, which includes:
an oily phase dispersed in an aqueous phase;
(i) at least one amphiphilic lipid selected from the group including nonionic amphiphilic lipids, anionic amphiphilic lipids, and combinations thereof; and
(ii) at least one water-soluble nonionic polymer selected from the group including homopolymers and copolymers of ethylene oxide; polyvinyl alcohols; homopolymers and copolymers of vinylpyrrolidone; homopolymers and copolymers of vinylcaprolactam; homopolymers and copolymers of polyvinyl methyl ether; neutral acrylic homopolymers and copolymers; $C_1$–$C_2$ alkyl celluloses and their derivatives; $C_1$–$C_3$ alkyl guar; $C_1$–$C_3$ hydroxyalkyl guar; and combinations thereof;
wherein a ratio of the weight of the oily phase to the weight of the amphiphilic lipid (i) ranges from 1.2 to 10;
and wherein the oily phase includes oil globules having a number-average size of less than 100 nm. The nanoemulsion obtained is preferably transparent and stable on storage. It may form a composition for topical, preferably cosmetic or dermatological compositions, pharmaceutical compositions and ophthalmological compositions.

33 Claims, No Drawings

NANOEMULSION CONTAINING NONIONIC POLYMERS, AND ITS USES

BACKGROUND OF THE INVENTION

1. Field of the Invention

The present invention relates to a nanoemulsion including at least one nonionic and/or anionic amphiphilic lipid and at least one neutral water-soluble polymer, and to the use of the said nanoemulsion in topical application, in particular in the cosmetic and dermatological fields and in the pharmaceutical and/or ophthalmological fields.

2. Discussion of the Background

Oil-in-water (O/W) emulsions are well known in the cosmetic and dermatological field, in particular for the preparation of cosmetic products such as milks, creams, tonics, serums and toilet waters.

Nanoemulsions are O/W emulsions wherein the size of the oily globules is less than 100 nm, and wherein the oily globules are stabilized by a wreath of amphiphilic lipids, which can optionally form a liquid crystal phase of lamellar type, situated at the oil/aqueous phase interface. The transparency of nanoemulsions originates from the small size of the oily globules, and the small size is obtained by virtue of mechanical energy and in particular the use of a high-pressure homogenizer during preparation. Nanoemulsions are distinguished from microemulsions by their structure. Microemulsions are thermodynamically stable dispersions composed of amphiphilic lipid micelles, which are swollen by oil. In contrast to nanoemulsions, microemulsions do not require high mechanical energy to be prepared; they are formed spontaneously by simply bringing the constituents into contact. The major disadvantages of microemulsions relate to their high proportion of surfactants, which result in intolerances and lead to a sticky feel when applied to the skin. The range of microemulsion formulation is generally very narrow, and their temperature stability is very limited.

Nanoemulsions include one or more amphiphilic lipid(s). The term "amphiphilic lipid" is understood to mean here any molecule having a bipolar structure, that is to say including at least one hydrophobic part and at least one hydrophilic part, and having the property of reducing the surface tension of water ($\gamma$<55 mN/m) and of reducing the interfacial tension between water and an oily phase. Synonyms for amphiphilic lipid include, for example: surfactant, surface-active agent, emulsifier.

EP-A-728 460 and EP-A-780 114 disclose nanoemulsions based on liquid nonionic amphiphilic lipids or on silicone surfactants. Nanoemulsions are also disclosed in FR-A-2 787 026, FR-A-2 787 027, FR-A-2 787 325, FR-A-2 787 326, FR-A-2 787 703 and FR-A-2 787 728.

In order for the nanoemulsions as disclosed in the above references to be used as milks or creams and in particular in the care field, they have to be rendered thicker and thus their viscosity has to be increased. There are two conventional ways to increase the viscosity of a nanoemulsion. The first way is to increase the fraction of the dispersed oily phase. This is because it is generally found that, from 22% by weight of oily phase with respect to the total weight of the composition, the viscosity increases as a function of the level of oil. This method, disclosed in the above-mentioned applications, makes it possible to obtain thick, transparent and stable compositions. However, such a method for thickening nanoemulsions is constrained by the need to have a high level of oil, which is not always desired as the formulas obtained are richer (high level of fatty phase), and the viscosity range is narrower.

The second way to increase the viscosity of a nanoemulsion is to add to the nanoemulsion a water-soluble polymer, which, by gelling of the continuous aqueous phase, will increase the viscosity of the combined mixture, even with low levels of oil. In the above-mentioned applications, the addition is envisaged of water-soluble polymers such as hydroxypropyl cellulose, algal derivatives, natural gums and synthetic polymers such as polymers and copolymers of carboxyvinyl acids, for example Carbopols which are anionic polymers. Unfortunately, the addition of such polymers affects the transparency of the products obtained; or else to keep the transparency, a small amount of polymer has to be introduced, which limits their effect in thickening the composition.

Thus, the need remains for a thickening system which makes it possible to suitably thicken a composition in the form of an oil-in-water nanoemulsion without influencing the cosmetic properties of the said compositions, in particular without influencing the transparent nature of the nanoemulsion, whatever the level of oil which it is desired to use.

SUMMARY OF THE INVENTION

Accordingly, it is an object of the present invention to provide a thickened oil-in-water nanoemulsion.

Another object of the invention is to provide a thickened oil-in-water nanoemulsion which retains the desirable properties of the nanoemulsion composition.

Another object of the invention is to provide a thickened oil-in-water nanoemulsion which retains the desirable cosmetic, dermatological, and/or ophthalmic properties of the nanoemulsion composition.

Another object of the invention is to provide a thickened oil-in-water nanoemulsion which is desirably transparent, whatever the level of oil which it is desired to use.

These objects and others may be accomplished with the present invention, the first embodiment of which provides an oil-in-water nanoemulsion, which includes:

an oily phase dispersed in an aqueous phase;

(i) at least one amphiphilic lipid selected from the group including nonionic amphiphilic lipids, anionic amphiphilic lipids, and combinations thereof; and (ii) at least one water-soluble nonionic polymer selected from the group including homopolymers and copolymers of ethylene oxide; polyvinyl alcohols; homopolymers and copolymers of vinylpyrrolidone; homopolymers and copolymers of vinylcaprolactam; homopolymers and copolymers of polyvinyl methyl ether; neutral acrylic homopolymers and copolymers; $C_1$–$C_2$ alkyl celluloses and their derivatives; $C_1$–$C_3$ alkyl guar; $C_1$–$C_3$ hydroxyalkyl guar; and combinations thereof;

wherein a ratio of the weight of the oily phase to the weight of the amphiphilic lipid (i) ranges from 1.2 to 10;

and wherein the oily phase includes oil globules having a number-average size of less than 100 nm.

Another embodiment of the present invention provides a cosmetic or dermatological composition, which includes the above-described nanoemulsion.

Another embodiment of the present invention provides an ophthalmic vehicle, which includes the above-described nanoemulsion.

Another embodiment of the present invention provides a pharmaceutical composition, which includes the above-described nanoemulsion.

Another embodiment of the present invention provides a method for caring for, treating, or making up the skin, face, or scalp, which includes applying the above-described nanoemulsion to the skin, face, or scalp.

Another embodiment of the present invention provides a method for caring for or treating the hair, which includes applying the above-described nanoemulsion to the hair.

Another embodiment of the present invention provides a method for caring for or moisturizing the skin, mucous membranes, or scalp, which includes applying the above-described nanoemulsion to the skin, mucous membranes, or scalp.

Another embodiment of the present invention provides a method of making a composition intended for the treatment of dry skin, which includes admixing the above-described nanoemulsion with the composition.

Another embodiment of the present invention provides a method of making an ophthalmological composition, which includes admixing the above-described nanoemulsion with the composition.

Another embodiment of the present invention provides a method for preparing the above-described nanoemulsion, which includes:

contacting the oily phase with the aqueous phase with high pressure homogenization to obtain a first nanoemulsion, and thereafter contacting the first nanoemulsion with the water-soluble nonionic polymer (ii) described above to obtain the above-described nanoemulsion.

Another embodiment of the present invention provides a method for thickening an oil-in-water nanoemulsion having oil globules whose number-average size is less than 100 nm, which includes contacting the nanoemulsion with at least one water-soluble nonionic polymer selected from the group including homopolymers and copolymers of ethylene oxide; polyvinyl alcohols; homopolymers and copolymers of vinylpyrrolidone; homopolymers and copolymers of vinylcaprolactam; homopolymers and copolymers of polyvinyl methyl ether; neutral acrylic homopolymers and copolymers; $C_1$–$C_2$ alkyl celluloses and their derivatives; $C_1$–$C_3$ alkyl guar; $C_1$–$C_3$ hydroxyalkyl guar; and combinations thereof.

Another embodiment of the present invention provides an oil-in-water nanoemulsion composition, which includes:

an oily phase dispersed in an aqueous phase;

(i) a means for emulsifying the composition; and (ii) a means for thickening the composition;

wherein a ratio of the weight of the oily phase to the weight of the means for emulsifying the composition ranges from 1.2 to 10;

and wherein the oily phase includes oil globules having a number-average size of less than 100 nm.

DESCRIPTION OF THE PREFERRED EMBODIMENTS

Various other objects, features and attendant advantages of the present invention will be more fully appreciated as the same becomes better understood from the following detailed description of the preferred embodiments of the invention.

The present inventors have discovered, unexpectedly, that it is possible to thicken nanoemulsions with certain water-soluble nonionic (neutral) polymers. These polymers are water-soluble and preferably completely free of hydrophobic chain.

One preferred embodiment of the present invention is an oil-in-water nanoemulsion including an oily phase dispersed in an aqueous phase, the oil globules of which have a number-average size of less than 100 nm, characterized in that it includes (i) at least one amphiphilic lipid chosen from nonionic amphiphilic lipids and anionic amphiphilic lipids, and (ii) at least one water-soluble nonionic polymer chosen from homopolymers and copolymers of ethylene oxide; polyvinyl alcohols; homopolymers and copolymers of vinylpyrrolidone; homopolymers and copolymers of vinylcaprolactam; homopolymers and copolymers of polyvinyl methyl ether; neutral acrylic homopolymers and copolymers; $C_1$–$C_2$ alkyl celluloses and their derivatives; $C_1$–$C_3$ alkyl guar or $C_1$–$C_3$ hydroxyalkyl guar, and in that the ratio by weight of the amount of oily phase to the amount of amphiphilic lipid ranges from 1.2 to 10, preferably from 2 to 10, and better still from 2 to 6 and even better from 3 to 6.

These polymers which are completely compatible with the nanoemulsions make it possible to thicken them or to cause them to gel in a wide range of viscosities, even for a small amount of oil, while maintaining good transparency of the nanoemulsions. They make it possible to increase the viscosity of the nanoemulsion by at least a factor of 5, for a polymer concentration equal to 1% by weight. They make it possible to obtain transparent and stable compositions constituting milks or creams. The term "milk" or "cream" is understood to mean compositions having a viscosity ranging from 1 to 200 Poises (i.e. 0.1 Pa.s to 20 Pa.s) measured at 25° C. with a Rheomat RM 180 with a 3, 4 or 5 rotor (according to the viscosity range) at 200 s$^{-1}$. These ranges expressly include 2, 5, 10, 20, 50, 75, 100, 125, 150, and 175 Poises.

Another preferred embodiment of the invention is a method for thickening an oil-in-water nanoemulsion having oil globules whose number-average size is less than 100 nm, which includes adding to the said nanoemulsion at least one water-soluble nonionic polymer chosen from homopolymers and copolymers of ethylene oxide; polyvinyl alcohols; homopolymers and copolymers of vinylpyrrolidone; homopolymers and copolymers of vinylcaprolactam; homopolymers and copolymers of polyvinyl methyl ether; neutral acrylic homopolymers and copolymers; $C_1$–$C_2$ alkyl celluloses and their derivatives; $C_1$–$C_3$ alkyl guar or $C_1$–$C_3$ hydroxyalkyl guar.

The nanoemulsions according to the invention generally have a transparent to bluish appearance. Their transparency is measured by a coefficient of transmission at 600 nm ranging from 10 to 90% or alternatively by turbidity. The turbidity of the compositions of the invention ranges from 60 to 400 NTU and preferably from 70 to 300 NTU, which turbidity is measured with a portable HACH—Model 2100 P turbidimeter at about 25° C. These ranges expressly include 20, 30, 40, 50, 60, 60, 70 and 80% and also 70, 100, 150, 200, 250, 300, 350 and 375 NTO.

The oil globules of the nanoemulsions of the invention have a number-average size of less than 100 nm and preferably ranging from 20 to 80 nm and more preferably from 40 to 60 nm. The decrease in the size of the globules makes it possible to promote the penetration of the active agents into the surface layers of the skin (vehicle effect). These ranges expressly include 2, 5, 10, 15, 25, 30, 50, 70 and 90 nm.

The nanoemulsions according to the invention are preferably prepared at temperatures ranging from 4 to 45° C. and are thus compatible with heat-sensitive active agents. This range expressly includes 5, 10, 20, 30, and 40° C.

The polymers used according to the present invention are water-soluble, that is to say are soluble in water, and are nonionic, that is to say neutral.

The water-soluble neutral polymers used according to the invention are chosen from the polymers described below and mixtures thereof.

A) homopolymers and copolymers of ethylene oxide, having a molar mass equal to or greater than 10,000 g/mol and preferably ranging from 10,000 g/mol to 10,000,000 g/mol. These ranges expressly include 20,000, 50,000, 100,000, 200,000, 500,000, 1,000,000 and 5,000,000 g/mol. They may be chosen from: (1) poly(ethylene oxides) having the following formula (I):

R—(CH$_2$—CH$_2$—O)$_n$-R'    (I)

in which R is chosen from the hydroxyl (OH), methoxy (OCH$_3$) and amine (NH$_2$) groups, R' is a methyl (CH$_3$) group or a hydrogen, and n is a number ranging from 220 to 230,000. This range expressly includes 500, 1,000, 5,000, 10,000, 100,000 and 200,000. (2) copolymers of ethylene oxide and of one or more oxyalkylenated monomers having the following formula (II):

—(CHR—CHR'—O)—    (II)

in which R and R', independently of each other, are hydrogen or an alkyl group including from 1 to 7 carbon atoms, at least one of R or R' being an alkyl group. This range expressly includes 2, 3, 4, 5, and 6 carbons.

Among the homopolymers and copolymers of ethylene oxide, there may be mentioned in particular the products marketed under the names Polyox Coagulant (molar mass of about 5×10$^6$ g/mol) (INCI name: PEG-115M) and Polyox WSR N-60K CG (INCI name: PEG-45M) (molar mass of about 2×10$^6$ g/mol) by the company Amerchol, as well as the product marketed under the name Carbowax 20M (INCI name: PEG-350) (molar mass of about 2×10$^7$ g/mol) by the company Union Carbide.

B) polyvinyl alcohols, in particular those having an average molar mass ranging from 10,000 g/mol to 500,000 g/mol. This range expressly includes 20,000, 50,000, 100,000, 200,000, 300,000 and 400,000 g/mol. These are compounds represented by the following formula (III):

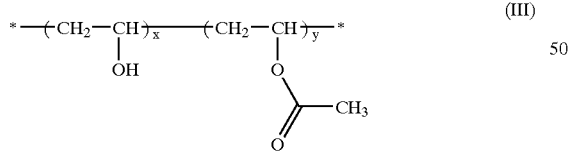

in which x is a mean number expressed as a percentage ranging from 70 to 100; y is a mean number equal to 100−x. The range for x expressly includes 75, 80, 85, 90 and 95.

There may be mentioned, for example, the products marketed under the names Airvols 103, 350, 203, 540, 714 and 603 by the company Air Products.

C) homopolymers and copolymers of vinylpyrrolidone, in particular those having an average molar mass ranging from 10,000 g/mol to 1,000,000 g/mol. This range expressly includes 15,000, 20,000, 75,000, 100,000, 500,000, and 750,000 g/mol. They may be chosen from:

1) polyvinylpyrrolidones having the following formula (IV):

There may be mentioned, for example, the products marketed under the names Polyclar V15 (molar mass of about 8000 g/mol), V30 (molar mass of about 50,000 g/mol), V60 (molar mass of about 400,000 g/mol), V90 (molar mass of about 1,000,000 g/mol) and V120 (molar mass of about 2,500,000 g/mol) by the company ISP.

2) copolymers of vinylpyrrolidone such as: (a) copolymers of vinylpyrrolidone and of vinyl acetate, in particular the copolymer containing 30% of vinyl acetate, marketed under the name PVP-VA 735 by the company ISP;

(b) copolymers of vinylpyrrolidone and of vinylpyrrolidone derivatives with butene grafts such as the copolymer containing 10% vinylpyrrolidone with butene grafts, marketed under the name Ganex (or Antaron) P904 by the company ISP;

(c) copolymers of vinylpyrrolidone and of maleic anhydride;

(d) copolymers of vinylpyrrolidone with polyvinyl alkyl ethers of the following formula (V):

in which R is chosen from the alkyl groups containing from 1 to 7 carbon atoms. This range expressly includes 2, 3, 4, 5, and 6 carbons. Preferably, R is a methyl group;

(e) copolymers of vinylpyrrolidone and of N-vinyllactams such as N-butyrolactam and N-vinylcaprolactam;

(f) copolymers of vinylpyrrolidone with the neutral acrylic derivatives of the following formula (VI):

in which R is hydrogen or a methyl group, and X is chosen from the groups alkyl oxide of the type OR' where R' contains from 1 to 7 carbon atoms (which range expressly includes 2, 3, 4, 5, and 6 carbons); hydroxylated and/or aminated alkyl oxide of the OR$_1$(OH)$_n$(NR$_2$R$_3$)$_m$ type where n and m are numbers ranging from 0 to 10 (which range expressly includes 1, 2, 3, 4, 5, 6, 7, 8 and 9), R$_1$ is an alkyl group containing from 1 to 7 carbon atoms (which range expressly includes 1, 2, 3, 4, 5, 6, 7, 8 and 9); R$_2$ and R$_3$ are independently hydrogen or an alkyl group such that the sum of the carbon atoms of R$_2$ and R$_3$ ranges from 1 to 7 (which range expressly includes 2, 3, 4, 5, and 6); primary, secondary or tertiary amine of the $NR_2R_3$ type where $R_2$ and $R_3$ have the meaning indicated above.

D) homopolymers and copolymers of vinyl caprolactam which may be chosen from: 1) polyvinylcaprolactams which have the following formula (VII):

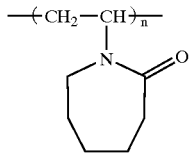

(VII)

2) copolymers of vinylcaprolactams obtained from vinylcaprolactam and from one or more of the following monomers:
   vinyl acetate;
   N-vinyllactam such as N-butyrolactam, N-vinylcaprolactam and N-vinylpyrrolidone;
   maleic anhydride;
   vinyl alkyl ethers of formula (V) indicated above;
   neutral acrylic derivatives of formula (VI) indicated above.

As polymers and copolymers of this type, there may be mentioned, for example, the product marketed under the name Luviskol Plus by the company BASF and the product marketed under the name H2OLD EP-1 by the company ISP.

E) homopolymers and copolymers of polyvinyl methyl ether which may be chosen from: 1) polyvinyl methyl ethers of formula (V) indicated above;

2) copolymers obtained from vinyl methyl ether and from one or more of the following monomers:
   vinyl alkyl ethers of formula (V) indicated above;
   vinyl acetate;
   N-vinyllactam such as N-butyrolactam, N-vinylcaprolactam and N-vinylpyrrolidone;
   maleic anhydride;
   neutral acrylic derivatives of formula (VI) indicated above.

As polymers and copolymers of this type, there may be mentioned, for example, the products marketed under the names Gantrez (INCI name: PVM/MA copolymer), and particularly Gantrez AN-119 (molar mass of about 190,000 g/mol), AN-139 (molar mass of about 950,000 g/mol), AN-149 (molar mass—1,100,000 g/mol), AN-169 (molar mass of about 1,700,000 g/mol) and AN-179 (molar mass of about 2,000,000 g/mol) by the company ISP.

F) neutral acrylic homopolymers and copolymers, in particular those having a molar mass ranging from 10,000 g/mol to 5,000,000 g/mol. This range expressly includes 20,000, 50,000, 100,000, 500,000, 1,000,000 and 2,500,000 g/mol. They may be chosen from:

1) neutral water-soluble acrylic polymers having the following formula (IX):

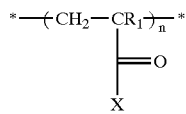

(IX)

in which $R_1$ is hydrogen or a methyl group, and X is chosen from (a) alkylamino groups or (b) hydroxylated and/or aminated alkyl oxide groups.

The polymers with (a) alkylamino groups are compounds of formula (IX) where $X=NR_2R_3$ such that the corresponding acrylic polymer is water-soluble, $R_2$ and $R_3$ being independently hydrogen or an alkyl group such that the sum of the carbon atoms of $R_2$ and $R_3$ ranges from 1 to 7 (which range expressly includes 2, 3, 4, 5, and 6). As polymers of this type, there may be mentioned in particular polyacrylamides where $R_1$, $R_2$ and $R_3$ are hydrogen; polymethylacrylamides where $R_1$ is a methyl group and $R_2$ and $R_3$ are hydrogen; poly-N-methylacrylamides where $R_1$ and $R_2$ are hydrogen and $R_3$ is a methyl group; poly-N,N'-dimethylacrylamides where $R_1$ is hydrogen and $R_2$ and $R_3$ are a methyl group; poly-N-ethylacrylamides where $R_1$ and $R_2$ are hydrogen and $R_3$ is an ethyl group; poly-N-isopropylacrylamides where $R_1$ and $R_2$ are hydrogen and $R_3$ is an isopropyl group.

As a polymer of this type, there may be mentioned the polyacrylamide marketed under the name Superfloc N300 LMW by the company Cytec.

Polymers with hydroxylated and/or aminated alkyl oxide groups (b) are compounds of formula (IX) in which $X=OR_2(OH)_n(NR_3R_4)_m$ where n and m are numbers ranging from 0 to 10 (which range expressly includes 1, 2, 3, 4, 5, 6, 7, 8, and 9), $R_2$ is an alkyl group containing from 1 to 7 carbon atoms (which range expressly includes 2, 3, 4, 5, and 6); $R_3$ and $R_4$ are independently hydrogen or an alkyl group such that the sum of the carbon atoms of $R_3$ and $R_4$ ranges from 1 to 7 (which range expressly includes 2, 3, 4, 5, and 6), these groups being such that the corresponding acrylic derivative is water-soluble.

As a polymer of this type, there may be mentioned the polyglyceryl methacrylate marketed under the name Lubrajel CG by the company Guardian.

2) copolymers of a water-soluble and neutral acrylic derivative of formula (IX) as defined above and of one or more of the following neutral monomers:
   vinyl acetate;
   N-vinyllactam such as N-butyrolactam, N-vinylcaprolactam and N-vinylpyrrolidone;
   maleic anhydride;
   vinyl alkyl ethers of formula (V) indicated above;
   neutral acrylic derivative of formula (VI) indicated above.

G) $C_1$–$C_2$ alkyl celluloses and their neutral derivatives, in particular those having a molar mass ranging from 10,000 g/mol to 5,000,000 g/mol. This range expressly includes 20,000, 50,000, 100,000, 500,000, 1,000,000 and 2,500,000 g/mol. They may be chosen in particular from hydroxyethyl cellulose such as the product marketed under the names Natrosols 250 LR and 250 HHR by the company Aqualon;

ethylhydroxyethyl cellulose such as the products marketed under the names Elfacos CD 481 and CD 411 by the company Akzo Nobel; methyl cellulose and methylhydroxyalkyl celluloses such as the product marketed under the name Methocel A4C by the company Dow Chemical and the products marketed under the names 10 Benecel by the company Hercules.

H) $C_1$–$C_3$ alkyl guar or $C_1$–$C_3$ hydroxyalkyl guar, in particular those having a molar mass ranging from 10,000 g/mol to 5,000,000 g/mol. This range expressly includes 20,000, 50,000, 100,000, 500,000, 1,000,000 and 2,500,000 g/mol. There may be mentioned hydroxypropyl guar such as the product marketed under the name Jaguar HP-105 by the company Rhodia. According to the invention, the water-soluble nonionic polymers may represent a quantity of 0.01 to 20% by weight, preferably of 0.05 to 10% by weight and more particularly of 0.1 to 5% by weight, relative to the total weight of the composition. These ranges expressly includes 0.5, 1, 2, 3, 9, 12, 15 and 18% by weight.

The nanoemulsions preferably include at least one amphiphilic lipid chosen from nonionic amphiphilic lipids, anionic amphiphilic lipids, as defined above, and their mixtures. The nonionic amphiphilic lipids of the invention are preferably chosen from:
1) silicone surfactants,
2) amphiphilic lipids which are liquid at a temperature of less than or equal to 45° C. chosen from esters of at least one polyol and of at least one fatty acid including at least one saturated or unsaturated and linear or branched, and in particular unsaturated or branched, $C_8$–$C_{22}$ alkyl chain, the polyol being chosen from the group formed by polyethylene glycol including from 1 to 60 ethylene oxide units, sorbitan, glycerol possibly including from 2 to 30 ethylene oxide units, and polyglycerols including from 2 to 15 glycerol units,
3) esters of fatty acid and of sugar and ethers of fatty alcohol and of sugar,
4) surfactants which are solid at a temperature of less than or equal to 45° C. chosen from glycerol fatty esters, sorbitan fatty esters and oxyethylenated sorbitan fatty esters, ethoxylated fatty ethers and ethoxylated fatty esters,
5) block copolymers of ethylene oxide (A) and of propylene oxide (B), and the mixtures of these surfactants.

1) The silicone surfactants which can be used according to the invention are silicone compounds including at least one oxyethylene —$OCH_2CH_2$— chain and/or oxypropylene —$OCH_2CH_2CH_2$— chain. Mention may be made, as silicone surfactants which can be used according to the present invention, of those disclosed in documents U.S. Pat. No. 5,364,633 and U.S. Pat. No. 5,411,744, the entire contents of each of which are hereby incorporated by reference.

The silicone surfactant used according to the present invention is preferably a compound of formula (X):

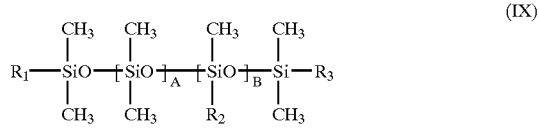

(IX)

in which:
$R_1$, $R_2$ and $R_3$, independently of one another, represent a $C_1$–$C_6$ alkyl radical or a —$(CH_2)_x$—$(OCH_2CH_2)_y$—$(OCH_2CH_2CH_2)_z$—$OR_4$ radical, at least one $R_1$, $R_2$ or $R_3$ radical not being an alkyl radical; $R_4$ being a hydrogen, an alkyl radical or an acyl radical;
A is an integer ranging from 0 to 200 (which range expressly includes 5, 20, 50, 100, and 150);
B is an integer ranging from 0 to 50 (which range expressly includes 5, 10, 25, 35, and 45);
provided that A and B are not equal to zero at the same time;
x is an integer ranging from 1 to 6 (which range expressly includes 2, 3, 4, and 5);
y is an integer ranging from 1 to 30 (which range expressly includes 5, 10, 15, 20 and 25);
z is an integer ranging from 0 to 5 (which range expressly includes 1, 2, 3, and 4).

According to a preferred embodiment of the invention, in the compound of formula (X), the alkyl radical is a methyl radical, x is an integer ranging from 2 to 6 and y is an integer ranging from 4 to 30.

Mention may be made, as examples of silicone surfactants of formula (X), of the compounds of formula (XI):

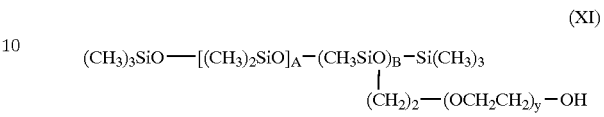

(XI)

in which A is an integer ranging from 20 to 105 (which range expressly includes 30, 40, 50, 75 and 100), B is an integer ranging from 2 to 10 (which range expressly includes 3, 4, 5, 6, 7 and 8) and y is an integer ranging from 10 to 20 (which range expressly includes 12, 14, 16, and 18).

Mention may also be made, as examples of silicone surfactants of formula (X), of the compounds of formula (XII):

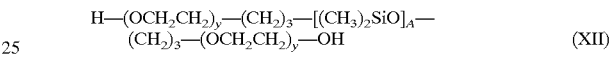

(XII)

in which A' and y are integers ranging from 10 to 20 (which range expressly includes 12, 14, 16, and 18).

Use may in particular be made, as silicone surfactants, of those sold by Dow Corning under the names DC 5329, DC 7439-146, DC 2-5695 and Q4-3667. The compounds DC 5329, DC 7439-146 and DC 2-5695 are compounds of formula (XI) where respectively A is 22, B is 2 and y is 12; A is 103, B is 10 and y is 12; A is 27, B is 3 and y is 12.

The compound Q4-3667 is a compound of formula (XII) where A is 15 and y is 13.

2) The amphiphilic lipids which are liquid at a temperature of less than or equal to 45° C. can be chosen in particular from:
polyethylene glycol isostearate with a molar weight of 400 (INCI name: PEG-8 Isostearate), sold under the name Prisorine 3644 by the company Unichema;
diglyceryl isostearate, sold by Solvay;
polyglyceryl laurate including 2 glycerol units (polyglyceryl-2 laurate), sold under the name diglycerin monolaurate by Solvay;
sorbitan oleate, sold under the name Span 80 by ICI;
sorbitan isostearate, sold under the name Nikkol SI 1OR by Nikko;
α-butylglucoside cocoate or a-butylglucoside caprate, sold by Ulice.

3) The esters of fatty acid and of sugar which can be used as nonionic amphiphilic lipids in the nanoemulsion according to the invention are preferably solid at a temperature of less than or equal to 45° C. and can be chosen in particular from the group including esters or mixtures of esters of $C_8$–$C_{22}$ fatty acid and of sucrose, of maltose, of glucose or of fructose and esters or mixtures of esters of $C_{14}$–$C_22$ fatty acid and of methylglucose.

The $C_8$–$C_{22}$ or $C_{14}$–$C_{22}$ fatty acids forming the fatty unit of the esters which can be used in the nanoemulsion of the invention include a saturated or unsaturated linear alkyl chain having from 8 to 22 or from 14 to 22 carbon atoms respectively (which ranges expressly include 10, 12, 16, 18 and 20 as appropriate). The fatty unit of the esters can be chosen in particular from stearates, behenates, arachidonates, palmitates, myristates, laurates, caprates and their mixtures. Stearates are preferably used.

Mention maybe made, as examples of esters or of mixtures of esters of fatty acid and of sucrose, of maltose, of glucose or of fructose, of sucrose monostearate, sucrose distearate, sucrose tristearate and their mixtures, such as the products sold by Croda under the name Crodesta F50, F70, F110 and F160 having respectively an HLB (Hydrophilic Lipophilic Balance) of 5, 7, 11 and 16; and, as examples of esters or of mixtures of esters of fatty acid and of methylglucose, of the distearate of methylglucose and of polyglycerol-3, sold by Goldschmidt under the name of Tego-care 450. Mention may also be made of glucose or maltose monoesters, such as methyl 0-hexadecanoyl6-D-glucoside and 0-hexadecanoyl-6-D-maltoside.

The ethers of fatty alcohol and of sugar which can be used as nonionic amphiphilic lipids in the nanoemulsion according to the invention are solid at a temperature of less than or equal to 45° C. and can be chosen in particular from the group including ethers or mixtures of ethers of $C_8$–$C_{22}$ fatty alcohol and of glucose, of maltose, of sucrose or of fructose and ethers or mixtures of ethers of $C_{14}$–$C_{22}$ fatty alcohol and of methylglucose. They are in particular alkylpolyglucosides.

The $C_8$–$C_{22}$ or $C_{14}$–$C_{22}$ fatty alcohols forming the fatty unit of the ethers which can be used in the nanoemulsion of the invention include a saturated or unsaturated linear alkyl chain having from 8 to 22 or from 14 to 22 carbon atoms respectively (which ranges expressly include 10, 12, 16, 18 and 20 as appropriate). The fatty unit of the ethers can be chosen in particular from the decyl, cetyl, behenyl, arachidyl, stearyl, palmityl, myristyl, lauryl, capryl or hexadecanoyl units and their mixtures, such as cetearyl.

Mention may be made, as examples of ethers of fatty alcohol and of sugar, of alkylpolyglucosides, such as decylglucoside and laurylglucoside, sold, for example, by Henkel under the respective names of Plantaren 2000 and Plantaren 1200, cetostearylglucoside, optionally as a mixture with cetostearyl alcohol, sold, for example, under the name Montanov 68 by Seppic, under the name Tego-care CG90 by Goldschmidt and under the name Emulgade KE3302 by Henkel, and arachidylglucoside, for example in the form of the mixture of arachidyl and behenyl alcohols and of arachidylglucoside sold under the name Montanov 202 by Seppic.

Use is more particularly made, as nonionic amphiphilic lipid of this type, of sucrose monostearate, sucrose distearate, sucrose tristearate and their mixtures, the distearate of methylglucose and of polyglycerol-3, and alkylpolyglucosides.

4) The glycerol fatty esters which can be used as nonionic amphiphilic lipids in the nanoemulsion of the invention, which are solid at a temperature of less than or equal to 45° C., can be chosen in particular from the group including the esters formed of at least one acid including a saturated linear alkyl chain having from 16 to 22 carbon atoms (which range expressly includes 18 and 20) and of 1 to 10 glycerol units (which range expressly includes 2, 3, 4, 5, 6, 7, 8 and 9). Use may be made of one or more of these glycerol fatty esters in the nanoemulsion of the invention.

These esters can be chosen in particular from stearates, behenates, arachidates, palmitates and their mixtures. Stearates and palmitates are preferably used.

Mention may be made, as examples of surfactant which can be used in the nanoemulsion of the invention, of decaglyceryl mono stearate, distearate, tristearate and pentastearate (10 glycerol units) (INCI names: Polyglyceryl-10 stearate, Polyglyceryl-10 distearate, Polyglyceryl-1 0 tristearate and Polyglyceryl-10 pentastearate), such as the products sold under the respective names Nikkol Decaglyn 1-S, 2-S, 3-S and 5-S by Nikko, and diglyceryl monostearate (INCI name: Polyglyceryl-2 stearate), such as the product sold by Nikko under the name Nikkol DGMS.

The sorbitan fatty esters which can be used as nonionic amphiphilic lipids in the nanoemulsion according to the invention, which are solid at a temperature of less than or equal to 45° C., are chosen in particular from the group including esters of $C_{16}$–$C_{22}$ fatty acid and of sorbitan and oxyethylenated esters of $C_{16}$–$C_{22}$ fatty acid and of sorbitan. They are formed of at least one fatty acid including at least one saturated linear alkyl chain, having respectively from 16 to 22 carbon atoms, and of sorbitol or of ethoxylated sorbitol. The oxyethylenated esters generally include from 1 to 100 ethylene oxide units and preferably from 2 to 40 ethylene oxide (EO) units.

These esters can be chosen in particular from stearates, behenates, arachidates, palmitates and their mixtures. Stearates and palmitates are preferably used.

Mention may be made, as examples of sorbitan fatty ester and of oxyethylenated sorbitan fatty ester which can be used in the nanoemulsion of the invention, of sorbitan monostearate (INCI name: Sorbitan stearate), sold by ICI under the name Span 60, sorbitan monopalmitate (INCI name: Sorbitan palmitate), sold by ICI under the name Span 40, or sorbitan 20 EO tristearate (INCI name: Polysorbate 65), sold by ICI under the name Tween 65.

The ethoxylated fatty ethers which are solid at a temperature of less than or equal to 45° C. which can be used as nonionic amphiphilic lipids in the nanoemulsion according to the invention are preferably ethers formed of 1 to 100 ethylene oxide units and of at least one fatty alcohol chain having from 16 to 22 carbon atoms. The fatty chain of the ethers can be chosen in particular from the behenyl, arachidyl, stearyl or cetyl units and their mixtures, such as cetearyl. Mention may be made, as examples of ethoxylated fatty ethers, of the ethers of behenyl alcohol including 5, 10, 20 and 30 ethylene oxide units (INCI names: Beheneth-5, Beheneth-10, Beheneth-20 and Beheneth-30), such as the products sold under the names Nikkol BB5, BB10, BB20 and BB30 by Nikko, and the ether of stearyl alcohol including 2 ethylene oxide units (INCI name: Steareth-2), such as the product sold under the name Brij 72 by ICI.

The ethoxylated fatty esters which are solid at a temperature of less than or equal to 45° C. which can be used as nonionic amphiphilic lipids in the nanoemulsion according to the invention are esters formed of 1 to 100 ethylene oxide units and of at least one fatty acid chain including from 16 to 22 carbon atoms. The fatty chain of the esters can be chosen in particular from the stearate, behenate, arachidate or palmitate units and their mixtures. Mention may be made, as examples of ethoxylated fatty esters, of the ester of stearic acid including 40 ethylene oxide units, such as the product sold under the name Myrj 52 (INCI name: PEG-40 stearate) by ICI, and the ester of behenic acid including 8 ethylene oxide units (INCI name: PEG-8 behenate), such as the product sold under the name Compritol HD5 ATO by Gattefosse.

5) The block copolymers of ethylene oxide and of propylene oxide, which can be used as nonionic amphiphilic lipids in the nanoemulsion according to the invention can be chosen in particular from the block copolymers of formula (XIII):

$$HO(C_2H_4O)_x(C_3H_6O)_y(C_2H_4O)_zH \qquad (XIII)$$

in which x, y and z are integers such that x+z ranges from 2 to 100 (which range expressly includes 5, 10, 20, 40, 60, and 80) and y ranges from 14 to 60 (which range expressly includes 16, 18, 20, 30, 40 and 50), and their mixtures and more particularly from the block copolymers of formula (V) having an HLB ranging from 2 to 16 (which range expressly includes 4, 6, 8, 10, 12, and 14).

These block copolymers can be chosen in particular from poloxamers and in particular from Poloxamer 231, such as the product sold by ICI under the name Pluronic L81 of formula (XIII) with x=z=6, y=39 (HLB 2); Poloxamer 282, such as the product sold by ICI under the name Pluronic L92 of formula (XIII) with x=z=10, y=47 (HLB 6); and Poloxamer 124, such as the product sold by ICI under the name Pluronic L44 of formula (XIII) with x=z=11, y=21 (HLB 16).

Mention may also be made, as nonionic amphiphilic lipids, of the mixtures of nonionic surfactants disclosed in EP-A-705593, incorporated herein by reference in its entirety.

Use may in particular be made, among nonionic amphiphilic lipids, of:
PEG 400 isostearate or PEG-8 isostearate (including 8 mol of ethylene oxide),
diglyceryl isostearate,
polyglyceryl monolaurate including 2 glycerol units and polyglyceryl stearates including 10 glycerol units,
sorbitan oleate,
sorbitan isostearate,
and their mixtures.

The anionic amphiphilic lipids which can be used in the nanoemulsions of the invention can be chosen from:
1) mixed esters of fatty acid or of fatty alcohol, of carboxylic acid and of glycerol,
2) alkyl ether citrates,
3) alkenyl succinates chosen from alkoxylated alkenyl succinates, alkoxylated glucose alkenyl succinates and alkoxylated methylglucose alkenyl succinates,
4) phosphoric acid fatty esters.

1) The mixed esters of fatty acid or of fatty alcohol, of carboxylic acid and of glycerol which can be used as anionic amphiphilic lipids in the nanoemulsion according to the invention can be chosen in particular from the group including mixed esters of fatty acid or of fatty alcohol having an alkyl chain including from 8 to 22 carbon atoms and of α-hydroxy acid and/or of succinic acid with glycerol. The α-hydroxy acid can be, for example, citric acid, lactic acid, glycolic acid, malic acid and their mixtures.

The alkyl chain of the fatty acids or alcohols from which the mixed esters which can be used in the nanoemulsion of the invention derive can be saturated or unsaturated and linear or branched. It can in particular be stearate, isostearate, linoleate, oleate, behenate, arachidonate, palmitate, myristate, laurate, caprate, isostearyl, stearyl, linoleyl, oleyl, behenyl, myristyl, lauryl and capryl chains and their mixtures.

Mention may be made, as examples of mixed esters which can be used in the nanoemulsion of the invention, of the mixed ester of glycerol and of the mixture of citric, lactic, linoleic and oleic acids (INCI name: Glyceryl citrate/lactate/linoleate/oleate) sold by Hills under the name Imwitor 375; the mixed ester of succinic acid and of isostearyl alcohol with glycerol (INCI name: Isostearyl diglyceryl succinate) sold by Huls under the name Imwitor 780 K; the mixed ester of citric acid and of stearic acid with glycerol (INCI name: Glyceryl stearate citrate) sold by Hills under the name Imwitor 370; or the mixed ester of lactic acid and of stearic acid with glycerol (INCI name: Glyceryl stearate lactate) sold by Danisco under the name Lactodan B30 or Rylo LA30.

2) The alkyl ether citrates which can be used as anionic amphiphilic lipids in the nanoemulsion according to the invention can be chosen in particular from the group including the monoesters, diesters or triesters formed by citric acid and at least one oxyethylenated fatty alcohol, including a saturated or unsaturated and linear or branched alkyl chain having from 8 to 22 carbon atoms and including from 3 to 9 ethoxylated groups, and their mixtures. This is because it is possible to use a mixture of one or more of these citrates in the nanoemulsion of the invention.

These citrates can be chosen, for example, from the mono-, di- and triesters of citric acid and of ethoxylated lauryl alcohol, including from 3 to 9 ethoxylated groups, sold by Witco under the name Witconol EC, in particular Witconol EC 2129, which is predominantly a dilaureth-9 citrate, and Witconol EC 3129, which is predominantly a trilaureth-9 citrate.

The alkyl ether citrates used as anionic amphiphilic lipids are preferably employed in the form neutralized to a pH of approximately 7, the neutralizing agent being chosen from inorganic bases, such as sodium hydroxide, potassium hydroxide or ammonia, and organic bases, such as mono-, di- and triethanolamine, aminomethylpropane-1,3-diol, N-methylglucamine or basic amino acids, such as arginine and lysine, and their mixtures.

3) The alkenyl succinates which can be used as anionic amphiphilic lipids in the nanoemulsion of the invention are in particular ethoxylated and/or propoxylated derivatives and they are preferably chosen from the compounds of formulae (XIV) or (XV):

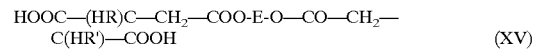

in which:
the R and R' radicals are chosen from linear or branched alkyl radicals including from 6 to 22 carbon atoms (which range expressly includes 10, 12, 14, 16, 18, and 20),
E is chosen from oxyethylene chains of formula $(C_2H_4O)_n$ in which n ranges from 2 to 100 (which range expressly includes 10, 20, 40, 60, 80 and 90), oxypropylene chains of formula $(C_3H_6O)_{n'}$, in which n' ranges from 2 to 100 (which range expressly includes 5, 10, 20, 30, 40, 50, 60, 70, 80 and 90), random or blocked copolymers including 5 oxyethylene chains of formula $(C_2H_4O)_{n'}$, and oxypropylene chains of formula $(C_3H_6O)_{n'}$ such that the sum of n and n' ranges from 2 to 100 (which range expressly includes 5, 10, 20, 30, 40, 50, 60, 70, 80 and 90), oxyethylenated and/or oxypropylenated glucose groups including, on average, from 4 to 100 oxyethylene and/or oxypropylene units distributed over all the hydroxyl functional groups, or oxyethylenated and/or oxypropylenated methylglucose groups including, on average, from 4 to 100 oxyethylene and/or oxypropylene units distributed over all the hydroxyl functional groups (which ranges expressly include 5, 10, 20, 30, 40, 50, 60, 70, 80 and 90).

In the formulae (XIV) and (XV), n and n' are mean values and are therefore not necessarily integers. The choice is advantageously made, for n, of a value ranging from 5 to 60 and more preferably still from 10 to 30.

The R and/or R' radical is advantageously chosen from linear alkyl radicals including from 8 to 22 and preferably from 14 to 22 carbon atoms (which ranges expressly include 10, 12, 14, 16, 18 and 20 carbons as appropriate). Preferably, it can be, for example, the hexadecenyl radical, including 16 carbon atoms, or the octadecenyl radical, including 18 carbon atoms.

The compounds of formulae (XIV) and (XV) described above in which E is chosen from oxyethylene chains, oxypropylene chains and copolymers including oxyethylene chains and oxypropylene chains can be prepared in accordance with the description which is given in documents WO-A-94/00508, EP-A-1 071 99 and GB-A-2 131 820, the entire contents of each of which are incorporated herein by reference.

The acid functional group —COOH of the anionic amphiphilic lipids of formulae (XIV) and (XV) is generally found in the nanoemulsion of the invention in the form neutralized by a neutralizing agent, the neutralizing agent being chosen, for example, from inorganic bases, such as sodium hydroxide, potassium hydroxide or ammonia, and organic bases, such as mono-, di- and triethanolamine, aminomethylpropane-1,3-diol, N-methylglucamine or basic amino acids, such as arginine and lysine, and their mixtures.

Mention may be made, as examples of anionic amphiphilic lipid of this type which can be used in the nanoemulsion of the invention, of hexadecenyl succinate 18 EO (compound of formula XIV with R=hexadecenyl, E=$(C_2H_4O)_n$ and n=18), hexadecenyl succinate 45 EO (compound of formula XIV with R=hexadecenyl, E=$(C_2H_4O)_n$ and n=45), dihexadecenyl succinate 18 EO (compound of formula XV with R=R'=hexadecenyl, E=$(C_2H_4O)_n$ and n=18), dihexadecenyl succinate of glucose 10 EO (compound of formula XV with R=R'=hexadecenyl and E=oxyethylenated glucose including 10 oxyethylene groups), dihexadecenyl succinate of glucose 20 EO (compound of formula XV with R=R'=hexadecenyl and E=oxyethylenated glucose including 20 oxyethylene groups), dioctadecenyl succinate of methylglucose 20 EO (compound of formula XV with R=R'=octadecenyl and E=oxyethylenated methylglucose including 20 oxyethylene groups), and their mixtures.

4) The phosphoric acid fatty esters and their oxyethylenated derivatives which can be used as anionic amphiphilic lipids in the nanoemulsion according to the invention can be chosen in particular from the group including the esters formed of phosphoric acid and of at least one alcohol including a saturated or unsaturated and linear or branched alkyl chain having from 8 to 22 carbon atoms (which range expressly includes 10, 12, 14, 16, 18 and 20) and the esters formed of phosphoric acid and of at least one ethoxylated alcohol including a saturated or unsaturated and linear or branched alkyl chain having from 8 to 22 carbon atoms (which range expressly includes 10, 12, 14, 16, 18 and 20) and including from 2 to 40 oxyethylene groups (which range expressly includes 4, 6, 8, 10, 12, 14, 16, 18, 20 and 30), their salts and their mixtures. This is because it is possible to use a mixture of one or more of these phosphoric acid esters in the nanoemulsion of the invention.

These esters can be chosen in particular from esters of phosphoric acid and of $C_9$–$C_{15}$ alcohols or their salts, such as the potassium salt of $C_9$–$C_{15}$ alkyl phosphate sold under the name Arlatone MAP by ICI; esters of phosphoric acid and of stearyl and/or isostearyl alcohols, such as the phosphate of stearyl/isostearyl alcohols (INCI name: Octyldecyl phosphate) sold under the name Hostaphat CG120 by Hoechst Celanese; esters of phosphoric acid and of cetyl alcohol, and their oxyethylenated derivatives, such as the product sold under the name Crodafos CES (mixture of cetearyl alcohol, of dicetyl phosphate and of ceteth-10 phosphate) by Croda; or esters of phosphoric acid and of tridecyl alcohol, and their oxyethylenated derivatives, such as the product sold under the name Crodafos T10 (INCI name: Trideceth-10 phosphate) by Croda. The oxyethylenated derivatives of phosphoric acid and of fatty alcohol can be prepared in accordance with the description given in Patent Application WO-A-96/14145, the entire contents of which is incorporated in the present application by reference.

These phosphoric acid fatty esters are preferably employed in the form neutralized to a pH of approximately 7, the neutralizing agent being chosen from inorganic bases, such as sodium hydroxide, potassium hydroxide or ammonia, and organic bases, such as mono-, di- and triethanolamine, aminomethylpropane-1,3-diol, N-methylglucamine or basic amino acids such as arginine and lysine, and their mixtures.

According to whether it is more hydrophilic or more lipophilic in nature, the nonionic or anionic amphiphilic lipid can be introduced into the aqueous phase or into the oily phase of the nanoemulsion. The amount of amphiphilic lipid ranges from 0.2 to 15% by weight and preferably from 1 to 10% by weight with respect to the total weight of the nanoemulsion.

The ratio by weight of the amount of the oily phase to the amount of amphiphilic lipid ranges from 1.2 to 10 and preferably from 1.2 to 6 (which ranges expressly include 1.3, 1.4, 1.5, 1.8, 2, 3, 4, 5, 7, 8 and 9). The term "amount of oily phase" is understood here to mean the total amount of the constituents of this phase, without including the amount of amphiphilic lipid.

According to a specific embodiment of the invention, the nanoemulsion of the invention can moreover include one or more additional ionic (anionic or cationic) amphiphilic lipids. Their addition, as additive, may further improve the stability of the dispersion. Preferably the additional anionic lipids may be present in the nanoemulsions based on neutral or anionic lipids, and the additional cationic lipids in the nanoemulsions based on neutral lipids.

Thus, the additional anionic amphiphilic lipids which can be used in the nanoemulsions of the invention are preferably chosen from:

alkaline salts of dicetyl and dimyristyl phosphate;
alkaline salts of cholesterol sulfate;
alkaline salts of cholesterol phosphate;
lipoamino acids and their salts, such as mono- and disodium acylglutamates, for instance the disodium salt of N-stearoyl-L-glutamic acid sold under the name Acylglutamate HS21 by Ajinomoto;
sodium salts of phosphatidic acid;
phospholipids;
alkylsulfonic derivatives, in particular of formula (XVI)

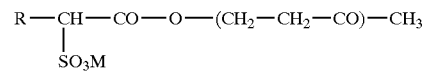

(XVI)

in which R represents $C_{16}$–$C_{22}$ alkyl radicals, in particular the $C_{16}H_{33}$ and $C_{18}H_{37}$ radicals taken as a mixture or separately, and M is an alkali metal or an alkaline earth metal, such as sodium; and their mixtures.

The cationic amphiphilic lipids which may be used in the nanoemulsions of the invention are preferably chosen from the group formed by quaternary ammonium salts, fatty amines and salts thereof.

The quaternary ammonium salts are, for example:
those which have the following general formula (XVII):

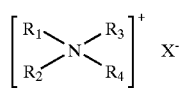
(XVII)

in which the radicals $R_1$ to $R_4$, which may be identical or different, represent a linear or branched aliphatic radical containing from 1 to 30 carbon atoms (which range expressly includes 2, 4, 6, 8, 10, 15, 20, and 25), or an aromatic radical such as aryl or alkylaryl. The aliphatic radicals may contain heteroatoms such as in particular oxygen, nitrogen, sulfur or halogens. The aliphatic radicals are, for example, chosen from the alkyl, alkoxy, polyoxy $(C_2–C_6)$alkylene, alkylamide, $(C_{12}–C_{22})$ alkylamido $(C_2–C_6)$ alkyl, $(C_{12}–C_{22})$ alkyl acetate or hydroxyalkyl radicals containing from about 1 to 30 carbon atoms (which range expressly includes 2, 4, 6, 8, 10, 15, 20, and 25); X is an anion chosen from the group including halides, phosphates, acetates, lactates, $(C_2–C_6)$ alkyl sulfates and alkyl- or alkylarylsulfonates,
the quaternary ammonium salts of imidazolinium, such as for example that of the following formula (XVIII):

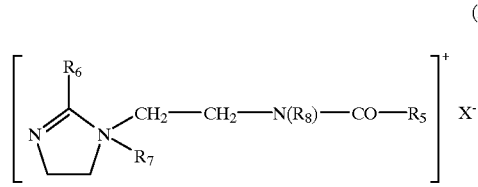
(XVIII)

in which $R_5$ represents an alkenyl or alkyl radical containing from 8 to 30 carbon atoms (which range expressly includes 10, 12, 14, 16, 18, 20, 22 and 26) which are for example derived from tallow fatty acids, $R_6$ represents a hydrogen atom, a $C_1–C_4$ alkyl radical or an alkenyl or alkyl radical containing from 8 to 30 carbon atoms (which range expressly includes 10, 12, 14, 16, 18, 20, 22 and 26), $R_7$ represents a $C_1–C_4$ alkyl radical, $R_8$ represents a hydrogen atom, a $C_1–C_4$ alkyl radical, X is an anion chosen from the group including the halides, phosphates, acetates, lactates, alkyl sulfates, alkyl- or alkylarylsulfonates. Preferably, $R_5$ and $R_6$ designate a mixture of alkenyl or alkyl radicals containing from 12 to 21 carbon atoms which are for example derived from tallow fatty acids, $R_7$, designates methyl and $R_8$ designates hydrogen. Such a product is for example marketed under the name "REWOQUAT W 75" by the company REWO.

Among the quaternary ammonium salts of formula (XVII), there are preferred, on the one hand, the tetraalkylammonium chlorides such as for example the dialkyldimethylammonium or alkyltrimethylammonium chlorides, in which the alkyl radical contains from about 12 to 22 carbon atoms (which range expressly includes 14, 16, 18, and 22), in particular the behenyltrimethylammonium, distearyldim-ethylammonium, cetyltrimethylammonium and benzyldimethylstearyl-ammonium chlorides or alternatively, on the other hand, the stearamidopropyldimethyl(myristyl acetate) ammonium chloride marketed under the name "CERAPHYL 70" by the company VAN DYK. The behenyltrimethylammonium chloride is the quaternary ammonium salt most particularly preferred.

the quaternary diammonium salts of formula (XIX):

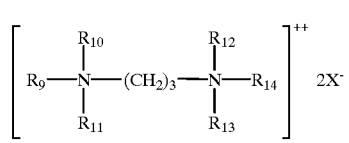
(XIX)

in which $R_9$ designates an aliphatic radical containing from about 16 to 30 carbon atoms, $R_{10}$, $R_{11}$, $R_{12}$, $R_{13}$ and
the saturated or unsaturated, linear or branched $C_1–C_6$ hydrocarbon radicals $R_{22}$,
the hydrogen atom,
$R_{17}$, $R_{19}$ and $R_{21}$, which are identical or different, are chosen from the saturated or unsaturated, linear or branched $C_7–C_{21}$ hydrocarbon radicals;
n, p and r, which are identical or different, are integers having values from 2 to 6 (which range expressly includes 3, 4, and 5);
y is an integer having a value from 1 to 10 (which range expressly includes 2, 3, 4, 5, 6, 7, 8, and 9);
x and z, which are identical or different, are integers having values from 0 to 10 (which range expressly includes 1, 2, 3, 4, 5, 6, 7, 8, and 9);
$X^-$ is an organic or inorganic, simple or complex anion (such as those described herein above and below);

with the proviso that the sum x+y+z has a value from 1 to 15, that when x has a value of 0, then $R_{16}$ designates $R_{20}$, and that when z has a value of 0, then $R_{18}$ designates $R_{22}$.

The alkyl radicals $R_{15}$ may be linear or branched and more particularly linear.

Preferably, $R_{15}$ designates a methyl, ethyl, hydroxyethyl or dihydroxypropyl radical and more particularly a methyl or ethyl radical.

Advantageously, the sum x+y+z has a value from 1 to 10 (which range expressly includes 2, 3, 4, 5, 6, 7, 8 and 9).

When $R_{16}$ is a hydrocarbon radical $R_{20}$, it may be long and may have from 12 to 22 carbon atoms (which range expressly includes 14, 16, 18, and 20), or may be short and may have from 1, 2, or 3 carbon atoms.

$R_{14}$, which are identical or different, are chosen from hydrogen or an alkyl radical containing from 1, 2, 3, or 4 carbon atoms, and X is an anion chosen from the group including the halides, acetates, phosphates, nitrates and methyl sulfates. Such quaternary diammonium salts include in particular propanetallowdiammonium dichloride.

the quaternary ammonium salts containing at least one ester functional group.

The quaternary ammonium salts containing at least one ester functional group which can be used according to the invention are for example those of the following formula (XX):

$$R_{17}-\overset{O}{\underset{\|}{C}}-(OC_nH_{2n})_y-\underset{\underset{R_{15}}{|}}{\overset{(C_rH_{2r}O)_z-R_{18}}{\overset{|}{N^+}}}-(C_pH_{2p}O)_xR_{16} \quad X^- \qquad (XX)$$

in which:

$R_{15}$ is chosen from $C_1$–$C_6$ alkyl radicals and $C_1$–$C_6$ hydroxyalkyl or dihydroxyalkyl radicals;

$R_{16}$ is chosen from:

$$R_{19}-\overset{O}{\underset{\|}{C}}-$$

the radical
the saturated or unsaturated, linear or branched $C_1$–$C_{22}$ hydrocarbon radicals $R_{20}$,
the hydrogen atom, $R_{18}$ is chosen from:

$$R_{21}-\overset{O}{\underset{\|}{C}}-$$

the radical
the saturated or unsaturated, linear or branched $C_1$–$C_6$ hydrocarbon radicals $R_{22}$,
the hydrogen atom, $R_{17}$, $R_{19}$ and $R_{21}$, which are identical or different, are chosen from the saturated or unsaturated, linear or branched $C_7$–$C_{21}$ hydrocarbon radicals;

n, p and r, which are identical or different, are integers having values from 2, 4, 5, or 6;

y is an integer having a value from 1 to 10 (which range expressly includes 2, 3, 4, 5, 6, 7, 8, and 9);

x and z, which are identical or different, are integers having values from 0 to 10 (which range expressly includes 1, 2, 3, 4, 5, 6, 7, 8, and 9);

$X^-$ is an organic or inorganic, simple or complex anion (such as those described hereinabove and below); with the proviso that the sum x+y+z has a value from 1 to 15, that when x has a value of 0, then $R_{16}$ designates $R_{20}$, and that when z has a value of 0, then $R_{18}$ designates $R_{22}$.

The alkyl radicals $R_{15}$ maybe linear or branched and more particularly linear.

Preferably, $R_{15}$ designates a methyl, ethyl, hydroxyethyl or dihydroxypropyl radical and more particularly a methyl or ethyl radical.

Advantageously, the sum x+y+z has a value from 1 to 10.

When $R_{16}$ is a hydrocarbon radical $R_{20}$, it may be long and may have from 12 to 22 carbon atoms (which range expressly includes 14, 16, 18 and 20), or may be short and may have from 1, 2, or 3 carbon atoms.

When $R_{18}$ is a hydrocarbon radical $R_{22}$, it preferably has 1 to 3 carbon atoms.

Advantageously, $R_{17}$, $R_{19}$ and $R_{21}$, which are identical or different, are chosen from saturated or unsaturated, linear or branched $C_{11}$–$C_{21}$ hydrocarbon radicals, and more particularly from saturated or unsaturated, linear or branched $C_{11}$–$C_{21}$ alkyl and alkenyl radicals.

Preferably, x and z, which are identical or different, have a value of 0 or 1.

Advantageously, y is equal to 1.

Preferably, n, p and r, which are identical or different, have a value of 2 or 3 and, still more particularly, are equal to 2.

In formula (XX), the anion is preferably a halide (chloride, bromide or iodide) or an alkyl sulfate, more particularly methyl sulfate. It is however possible to use methanesulfonate, phosphate, nitrate, tosylate, an organic acid-derived anion such as acetate or lactate or any other anion compatible with ammonium containing an ester functional group. The anion $X^-$ is still more particularly chloride or methyl sulfate.

Use is more particularly made of the ammonium salts of formula (XX) in which:

$R_{15}$ designates a methyl or ethyl radical,
x and y are equal to 1;
z is equal to 0 or 1;
n, p and rare equal to 2;
$R_{16}$ is chosen from:

$$R_{19}-\overset{O}{\underset{\|}{C}}-$$

the radical
the methyl, ethyl or $C_{14}$–$C_{22}$ hydrocarbon radicals
the hydrogen atom;

$R_{18}$ is chosen from:

$$R_{21}-\overset{O}{\underset{\|}{C}}-$$

the radical
the hydrogen atom;

$R_{17}$, $R_{19}$ and $R_{21}$, which are identical or different, are chosen from saturated or unsaturated, linear or branched $C_{13}$–$C_{17}$ hydrocarbon radicals and preferably from saturated or unsaturated, linear or branched $C_{13}$–$C_{17}$ alkyl and alkenyl radicals.

Advantageously, the hydrocarbon radicals are linear.

There may be mentioned for example as compounds of formula (XX) the salts (chloride or methyl sulfate in particular) of diacyloxyethyldimethylammonium, of diacyloxyethyl-hydroxyethylmethylammonium, of monoacyloxyethyl-dihydroxyethylmethylammonium, of triacyloxyethylmethylammonium, of monoacyloxyethylhydroxyethyldimethylammonium and mixtures thereof. The acyl radicals preferably have 14 to 18 carbon atoms and are more particularly obtained from a vegetable oil such as palm oil or sunflower oil. When the compound contains several acyl radicals, the latter may be identical or different. These products are obtained for example by direct esterification of triethanolamine, of triisopropanolamine, of alkyldiethanolamine or of alkyldiisopropanolamine which are optionally oxyalkylenated on fatty acids or on mixtures of fatty acids of plant or animal origin or by transesterification of methyl esters thereof. This esterification is followed by quaternization with the aid of an alkylating agent such as an alkyl (preferably methyl or ethyl) halide, a dialkyl (preferably methyl or ethyl) sulfate, methyl methanesulfonate, methyl para-toluenesulfonate, or glycol or glycerol chlorohydrin.

Such compounds are for example marketed under the names DEHYQUART by the company HENKEL, STEPANQUAT by the company STEPAN, NOXAMIUM by the company CECA, REWOQUAT WE 18 by the company REWO-WITCO.

The composition according to the invention, when it contains ammonium salts, preferably contains a mixture of quaternary ammonium mono-, di- and triester salts, with a majority by weight of diester salts.

As a mixture of ammonium salts, there may be used for example the mixture containing 15 to 30% by weight of acyloxyethyldihydroxyethylmethylammonium methyl sulfate, 45 to 60% of diacyloxyethyl-hydroxyethylmethylammonium methyl sulfate and 15 to 30% of triacyloxyethyl-methylammonium methyl sulfate, acyl radicals having from 14 to 18 carbon atoms and being obtained from optionally partially hydrogenated palm oil.

It is also possible to use the ammonium salts containing at least one ester functional group which are described in patents U.S. Pat. No. 4,874,554 and U.S. Pat. No. 4,137,180, the entire contents of each of which are hereby incorporated by reference.

When the nanoemulsion includes one or more additional ionic amphiphilic lipids, they are present in the nanoemulsions of the invention preferably in concentrations ranging from 0.01 to 10% by weight with respect to the total weight of the nanoemulsion and more particularly from 0.2 to 1% by weight (which ranges expressly include 0.05, 0.1, 2, 3, 4, 5, 6, 7, 8 and 9%).

The oily phase of the nanoemulsion according to the invention includes at least one oil. The oils which can be used in the nanoemulsions of the invention are preferably chosen from the group formed by:—oils of animal or vegetable origin, formed by esters of fatty acids and of polyols, in particular liquid triglycerides, for example sunflower, maize, soybean, avocado, jojoba, gourd, grape seed, sesame and hazelnut oils, fish oils or glyceryl tricaproaprylate, or vegetable or animal oils of formula $R_9COOR_{10}$ in which $R_9$ represents the residue of a higher fatty acid including from 7 to 29 carbon atoms and $R_{10}$ represents a linear or branched hydrocarbonaceous chain including from 3 to 30 carbon atoms, in particular an alkyl or alkenyl chain, for example Purcellin oil or liquid jojoba wax;

natural or synthetic essential oils, such as, for example, eucalyptus, lavandin, lavender, vetiver, litsea cubeba, lemon, santal, rosemary, camomile, savoury, nutmeg, cinnamon, hyssop, caraway, orange, geraniol, cade and bergamot oils;

synthetic oils, such as parleam oil, polyolefins and liquid carboxylic acid esters;

mineral oils, such as hexadecane, isohexadecane and liquid paraffin;

halogenated oils, in particular fluorocarbons, such as fluoroamines, for example perfluorotributylamine, fluorinated hydrocarbons, for example perfluorodecahydronaphthalene, fluoroesters and fluoroethers;

volatile or nonvolatile silicone oils.

The polyolefins which can be used as synthetic oils are in particular poly-α-olefins and more particularly those of hydrogenated or nonhydrogenated polybutene type and preferably hydrogenated or nonhydrogenated polyisobutene type.

The liquid carboxylic acid esters which can be used as synthetic oils can be esters of mono-, di-, tri- or tetracarboxylic acids. The total carbon number of the esters is generally greater than or equal to 10 and preferably less than 100 and more particularly less than 80. They are in particular monoesters of saturated or unsaturated and linear or branched $C_1$–$C_{26}$ aliphatic acids and of saturated or unsaturated and linear or branched $C_1$–$C_{26}$ aliphatic alcohols, the total carbon number of the esters generally being greater than or equal to 10. Use may also be made of esters of $C_4$–$C_{22}$ di- or tricarboxylic acids and of $C_1$–$C_{22}$ alcohols, and esters of mono-, di- or tricarboxylic acids and of C2–C26 di-, tri-, tetra- or pentahydroxyl alcohols.

It is preferable, among the above-mentioned esters, to use alkyl palmitates, such as ethyl palmitate, isopropyl palmitate, 2-ethylhexyl palmitate or 2-octyldecyl palmitate; alkyl myristates, such as isopropyl myristate, butyl myristate, cetyl myristate or 2-octyldodecyl myristate; alkyl stearates, such as hexyl stearate, butyl stearate or isobutyl stearate; alkyl malates such as dioctyl malate; alkyl laurates, such as hexyl laurate and 2-hexyldecyl laurate; isononyl isononanoate; or cetyl octanoate.

The nanoemulsions in accordance with the invention include an amount of oily phase (oil and other fatty substances apart from the amphiphilic lipid) preferably ranging from 2 to 40% by weight with respect to the total weight of the nanoemulsion and more particularly from 4 to 30% by weight and preferably from 4 to 20% by weight (which ranges expressly include 3, 5, 6, 8, 10, 12, 14, 16, 18, 22, 26, 32, and 36% by weight).

The nanoemulsions in accordance with the present invention can include solvents, in particular for improving, if necessary, the transparency of the composition.

These solvents are preferably chosen from the group formed by:

lower $C_1$–$C_8$ alcohols, such as ethanol;

glycols, such as glycerol, propylene glycol, 1,3-butylene glycol, dipropylene glycol or polyethylene glycols including from 4 to 16 ethylene oxide units and preferably from 8 to 12;

sugars, such as glucose, fructose, maltose, lactose or sucrose.

These additives can be used as a mixture. When they are present in the nanoemulsion of the invention, they can be used at concentrations preferably ranging from 0.01 to 30% by weight with respect to the total weight of the nanoemulsion and better still from 5 to 20% by weight with respect to the total weight of the nanoemulsion (which ranges expressly include 0.05, 1, 2, 3, 4, 6, 9, 10, 15, 25 and 28% by weight). The amount of alcohol(s) and/or of sugar(s) preferably ranges from 5 to 20% by weight with respect to the total weight of the nanoemulsion and the amount of glycol(s) preferably ranges from 5 to 15% by weight with respect to the total weight of the nanoemulsion (which ranges expressly include 6, 7, 8, 9, 10, 11, 12, 13, 14, 16, 17, 18 and 19% by weight).

The process for the preparation of a nanoemulsion as defined above includes mixing the aqueous phase and the oily phase, with vigorous stirring, at an ambient temperature of less than 45° C., in carrying out a stage of high-pressure homogenization at a pressure of greater than $5 \times 10^7$ Pa and then adding the polymer used according to the invention. According to a preferred embodiment of the invention, a further stage of high-pressure homogenization is subsequently carried out at a pressure of greater than $5 \times 10^7$ Pa. The high-pressure homogenization is preferably carried out at a pressure ranging from $6 \times 10^7$ to $18 \times 10^7$ Pa. The shearing preferably ranges from $2 \times 10^6$ s$^{-1}$ to $5 \times 10^8$ s$^{-1}$ and better still from $1 \times 10^8$ s$^{-1}$ to $3 \times 10^8$ s$^{-1}$ (s$^{-1}$ means second$^{-1}$). Such a process makes it possible to prepare, at ambient temperature, nanoemulsions which are compatible with heat-sensitive active compounds and which can include oils and in particular fragrances which include fatty substances, without denaturing them.

The nanoemulsions defined above can be used in any field where this type of composition is of use. They can constitute in particular compositions for topical use and in particular cosmetic or dermatological compositions, according to the type of active principles and the amount of these active principles included therein. They can also be used as ophthalmic vehicles. In addition, they can constitute, in the pharmaceutical field, the vehicle for a pharmaceutical composition which can be administered orally, parenterally or transcutaneously.

Such a composition for topical, pharmaceutical or ophthalmic use includes a physiologically acceptable medium, that is to say a medium compatible with the skin, mucous membranes, scalp, eyes and/or hair.

Another subject of the invention is an ophthalmic vehicle, characterized in that it includes a nanoemulsion as defined above.

Another subject of the invention is a pharmaceutical composition, characterized in that it includes a nanoemulsion as defined above.

Another subject of the invention is a cosmetic or dermatological composition, characterized in that it is composed of a nanoemulsion or includes a nanoemulsion as defined above.

The compositions of the invention can include adjuvants and in particular water-soluble or fat-soluble active principles having a cosmetic or dermatological activity. The fat-soluble active principles are in the oily globules of the emulsion, whereas the water-soluble active principles are in the aqueous phase of the emulsion. Mention may be made, as examples of active principle, of vitamins and their derivatives, such as vitamin E and its esters, such as vitamin E acetate, vitamin C and its esters, vitamins B, vitamin A alcohol or retinol and its esters, such as vitamin A palmitate, or vitamin A acid or retinoic acid and its derivatives, provitamins, such as panthenol, niacinamide or ergocalciferol, antioxidants, essential oils, humectants, sunscreen agents, moisturizing agents, proteins, ceramides and pseudoceramides, DHEA and its biological precursors and derivatives. Mention may be also be made, as adjuvants, of sequestering agents, softeners, coloring materials pigments or dyes) and fragrances.

Mention may be made, as ophthalmic active principles, of, for example, antiglaucoma agents, such as betaxolol; antibiotics, such as acyclovir; antiallergics; anti-inflammatory agents, such as ibuprofen and its salts, diclofenac and its salts, or indomethacin; or antiviral agents.

The amounts of these various adjuvants are those conventionally used in the field under consideration, for example from 0.01 to 20% of the total weight of the composition. These adjuvants and their concentrations must be such that they do not modify the property desired for the composition of the invention.

The nanoemulsion of the invention can be used, for example, for caring for, treating or making up the skin, the face and/or the scalp.

Another subject of the invention is therefore the cosmetic use of the nanoemulsion as defined above for caring for, treating and/or making up the skin, the face and/or the scalp.

In addition, the nanoemulsion of the invention can also be used for caring for and/or treating the hair. It makes it possible to obtain a deposit of oil on the hair which gives it greater sheen and renders it more resistant to styling, without, however, rendering it lank. It also makes it possible, in pretreatment, to improve the effects of dyeing or of permanent waving.

Another subject of the invention is thus the cosmetic use of the nanoemulsion as defined above for caring for and/or treating the hair.

The nanoemulsion according to the invention makes possible in particular good moisturizing of the skin, mucous membranes and/or scalp and is particularly suitable for the treatment of dry skin.

Another subject of the invention is thus a cosmetic process for caring for and/or moisturizing the skin, mucous membranes and/or scalp, characterized in that a nanoemulsion as defined above is applied to the skin, mucous membranes and/or scalp.

The invention also relates to the use of the nanoemulsion according to the invention in the manufacture of a composition intended for the treatment of dry skin.

Finally, the invention also relates to the use of the nanoemulsion according to the invention in the manufacture of an ophthalmological composition.

EXAMPLES

Having generally described this invention, a further understanding can be obtained by reference to certain specific examples which are provided herein for purposes of illustration only and are not intended to be limiting unless otherwise specified. The amounts shown are in % by weight, unless otherwise mentioned.

Example 1

Transparent Gelled Serum

| | |
|---|---|
| A. PEG 400 isostearate | 4.5% |
| Disodium acylglutamate | 0.5% |
| Isopropyl myristate | 5% |
| Isocetyl stearate | 10% |
| B. Dipropylene glycol | 10% |
| Glycerol | 5% |
| Distilled water | 32.5% |
| C. Poly(ethylene oxide) having a molar mass of 300,000 g/mol | 3% |
| Distilled water | 29.5% |

Procedure: The nanoemulsion is prepared in the high-pressure homogenizer from phases A and B. Phase C is prepared by stirring the polymer in water at 80° C. for 4 hours. After cooling to room temperature, phase C is introduced into the nanoemulsion while stirring with the defloculator.

A cream is obtained which has a turbidity of 288 NTU, a viscosity of 1.1 Pa.s (at 200 s$^{-1}$) This cream is stable and spreads easily over the skin.

Example 2

Transparent Gelled Serum

| | |
|---|---|
| A. PEG 400 isostearate | 4.5% |
| Disodium acylglutamate | 0.5% |
| Isopropyl myristate | 5% |
| Isocetyl stearate | 10% |

-continued

| | |
|---|---|
| B. Dipropylene glycol | 10% |
| Glycerol | 5% |
| Distilled water | 32.5 % |
| C. Hydroxypropyl guar (Jaguar HP-105) | 0.8% |
| Distilled water | 31.7% |

Procedure: The nanoemulsion is prepared in the high-pressure homogenizer from phases A and B. Phase C is prepared by stirring the polymer in water at 25° C. for 4 hours and is then introduced into the nanoemulsion while stirring with the deflocculator. The combined mixture is passed through the high-pressure homogenizer under the same conditions.

A transparent composition is obtained which has a turbidity of 250 NTU, a viscosity of 0.9 Pa.s (rotor 3, at 200 s$^{-1}$) and a pH of approximately 7. This composition spreads easily over the skin and is pleasant to use.

Example 3

| | |
|---|---|
| A. PEG 400 isostearate | 4.5% |
| Disodium acylglutamate | 0.5% |
| Isopropyl myristate | 5% |
| Isocetyl stearate | 10% |
| B. Dipropylene glycol | 10% |
| Glycerol | 5% |
| Distilled water | 44.9% |
| Preservative | 0.1% |
| C. Natrosol 250HHR | 0.5% |
| Distilled water | 19.5% |

The nanoemulsion is prepared in the high-pressure homogenizer from phases A and B. Phase C is prepared by stirring the polymer in water at 25° C. for 4 hours, and it is then introduced into the nanoemulsion while stirring with the deflocculator. The turbidity of the transparent composition obtained is 205 NTU, and its viscosity is 0.47 Pa.s (rotor 2, shearing speed=200 s$^{-1}$.

Comparative Example

| | |
|---|---|
| A. PEG 400 isostearate | 4.5% |
| Disodium acylglutamate | 0.5% |
| Isopropyl myristate | 5% |
| Isocetyl stearate | 10% |
| B. Dipropylene glycol | 10% |
| Glycerol | 5% |
| Distilled water | 45% |
| C. Carbopol 980 | 0.26% |
| Triethanolamine | 0.39% |
| Distilled water | 19.35% |

The nanoemulsion is prepared from phases A and B with the aid of a high-pressure homogenizer. Phase C is introduced into the nanoemulsion by stirring with the deflocculator. The formula obtained is white.

Obviously, numerous modifications and variations of the present invention are possible in light of the above teachings. It is therefore to be understood that within the scope of the appended claims, the invention may be practiced otherwise than as specifically described herein.

This application is based on French patent application 0009222, filed Jul. 13, 2000, the entire contents of which are hereby incorporated by reference, the same as if set forth at length.

The invention claimed is:

1. An oil-in-water nanoemulsion, comprising:
an oily phase dispersed in an aqueous phase;
(i) at least one amphiphilic lipid selected from the group consisting of nonionic amphiphilic lipids, anionic amphiphilic lipids, and combinations thereof; and
(ii) at least one water-soluble nonionic polymer selected from the group consisting of homopolymers and copolymers of ethylene oxide having a molar mass equal to or greater than 10,000 g/mol; polyvinyl alcohols; homopolymers and copolymers of vinylpyrrolidone; homopolymers and copolymers of vinylcaprolactam; homopolymers and copolymers of polyvinyl methyl ether; neutral acrylic homopolymers and copolymers; C1–C3 alkyl guar; C1–C3 hydroxyalkyl guar; and combinations thereof; wherein the at least one water-soluble nonionic polymer is free of hydrophobic chains;
wherein a ratio of the weight of said oily phase to the weight of said amphiphilic lipid (i) ranges from 1.2 to 10;
and wherein said oily phase comprises oil globules having a number-average size of less than 100 nm, wherein the water-soluble nonionic polymer is present in a nanoemulsion thickening effective amount.

2. The nanoemulsion according to claim 1, wherein said ratio ranges from 2 to 6.

3. The nanoemulsion according to claim 1, wherein the oil globules have a number-average size ranging from 20 to 80 nm.

4. The nanoemulsion according to claim 1, having a viscosity ranging from 1 to 200 Poises when measured at 25° C. at 200 s$^{-1}$.

5. The nanoemulsion according to claim 1, having a turbidity ranging from 60 to 400 NTU.

6. The nanoemulsion according to claim 1, wherein said nanoemulsion comprises at least one homopolymer or copolymer of ethylene oxide and said homopolymer or copolymer of ethylene oxide is selected from the group consisting of:

(1) poly(ethylene oxides) having the following formula (I):

$$R-(CH_2-CH_2-O)_n-R' \quad (I)$$

in which R is selected from the group consisting of hydroxyl, methoxy and amine group, R' is a methyl group or a hydrogen, and n is a number ranging from 220 to 230,000;

(2) copolymers of ethylene oxide and of one or more oxyalkylenated monomers having the following formula (II):

$$-(CHR-CHR'-O)- \quad (II)$$

in which R and R', independently of each other, are hydrogen or an alkyl group comprising from 1 to 7 carbon atoms, at least one of R or R' being an alkyl group; and (3) combinations thereof.

7. The nanoemulsion according to claim 1, wherein said nanoemulsion comprises at least one polyvinyl alcohol and said polyvinyl alcohol is a compound having the following formula (III):

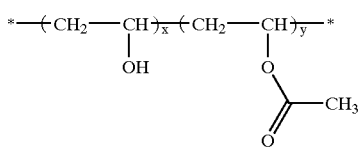
(III)

in which x is a mean number expressed as a percentage ranging from 70 to 100; and y is a mean number equal to 100−x.

8. The nanoemulsion according to claim 1, wherein said nanoemulsion comprises at least one homopolymer or copolymer of vinylpyrrolidone and said homopolymer or copolymer of vinylpyrrolidone is selected from the group consisting of:

polyvinylpyrrolidones having the following formula (IV):

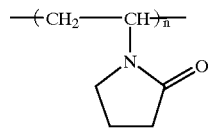
(IV)

copolymers of vinylpyrrolidone and vinyl acetate;
copolymers of vinylpyrrolidone and vinylpyrrolidone compounds having butene grafts;
copolymers of vinylpyrrolidone and malefic anhydride;
copolymers of vinylpyrrolidone with polyvinyl alkyl ethers of the following formula (V):

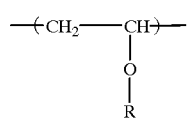
(V)

in which R is selected from the group consisting of alkyl groups having from 1 to 7 carbon atoms;
copolymers of vinylpyrrolidone and N-vinyllactams;
copolymers of vinylpyrrolidone with neutral acrylic derivatives of the following formula (VI):

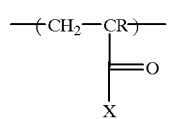
(VI)

in which R is hydrogen or a methyl group, and X is selected from the group consisting of alkyl oxide having the formula OR' where R' is an alkyl group having 1 to 7 carbon atoms; hydroxylated and/or aminated alkyl oxide having the formula $OR_1$ $(OH)_n(NR_2R_3)_m$ where n and m are each independently numbers ranging from 0 to 10, $R_1$ is an alkyl group having 1 to 7 carbon atoms; $R_2$ and $R_3$ are each independently hydrogen or an alkyl group such that the sum of the carbon atoms of $R_2$ and $R_3$ ranges from 1 to 7; primary, secondary or tertiary amine having the formula $NR_2R_3$ where $R_2$ and $R_3$ have the meaning indicated above.

9. The nanoemulsion according to claim 1, wherein said nanoemulsion comprises at least one homopolymer or copolymer of vinylcaprolactam and said homopolymer or copolymer of vinylcaprolactam is selected from the group consisting of:

(1) polyvinylcaprolactams which have the following formula (VII):

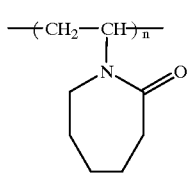
(VII)

(2) copolymers of vinylcaprolactams obtained from vinylcaprolactam and one or more of the following monomers:
vinyl acetate;
N-vinyllactam;
maleic anhydride;
vinyl alkyl ethers of formula (V);

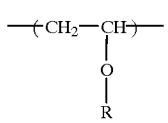
(V)

in which R is selected from the group consisting of alkyl groups containing from 1 to 7 carbon atoms;
neutral acrylic derivatives of formula (VI)

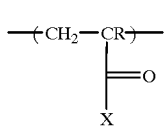
(VI)

in which R is hydrogen or a methyl group, and X is selected from the group consisting of alkyl oxide having the formula OR' where R' is an alkyl group having 1 to 7 carbon atoms; hydroxylated and/or aminated alkyl oxide having the formula $OR_1$ $(OH)_n(NR_2R_3)_m$ where n and m are each independently numbers ranging from 0 to 10, $R_1$ is an alkyl group having 1 to 7 carbon atoms; $R_2$ and $R_3$ are each independently hydrogen or an alkyl group such that the sum of the carbon atoms of $R_2$ and $R_3$ ranges from 1 to 7; primary, secondary or tertiary amine having the formula $NR_2R_3$ where $R_2$ and $R_3$ have the meaning indicated above; and (3) combinations thereof.

10. The nanoemulsion according to claim 1, wherein said nanoemulsion comprises at least one copolymer of polyvinyl methyl ether and said copolymer of polyvinyl methyl ether is a copolymer of vinyl methyl ether and one or more of the following monomers:

vinyl alkyl ethers of formula (V):

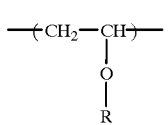

(V)

in which R is selected from the group consisting of alkyl groups containing from 1 to 7 carbon atoms;
vinyl acetate;
N-vinyllactam;
maleic anhydride; and
neutral acrylic derivatives of formula (VI):

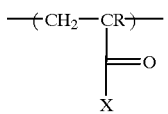

(VI)

in which R is hydrogen or a methyl group, and X is selected from the group consisting of alkyl oxide having the formula OR' where R' is an alkyl group having 1 to 7 carbon atoms; hydroxylated and/or aminated alkyl oxide having the formula $OR_1(OH)_n(NR_2R_3)_m$ where n and m are each independently numbers ranging from 0 to 10, $R_1$ is an alkyl group having 1 to 7 carbon atoms; $R_2$ and $R_3$ are each independently hydrogen or an alkyl group such that the sum of the carbon atoms of $R_2$ and $R_3$ ranges from 1 to 7; and primary, secondary or tertiary amine having the formula $NR_2R_3$ where $R_2$ and $R_3$ have the meaning indicated above.

11. The nanoemulsion according to claim 1, wherein said nanoemulsion comprises at least one neutral acrylic copolymer or homopolymer and said neutral acrylic copolymer or homopolymer is selected from the group consisting of:
neutral water-soluble acrylic polymers having the following formula (IX):

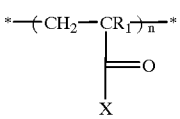

(IX)

in which $R_1$ is hydrogen or a methyl group, and X is selected from the group consisting of (a) and (b):
(a) alkylamino groups having the formula $NR_2R_3$, wherein $R_2$ and $R_3$ are each independently hydrogen or an alkyl group such that the sum of the carbon atoms of $R_2$ and $R_3$ ranges from 1 to 7, and wherein the resulting acrylic polymer is water-soluble; and
(b) hydroxylated and/or aminated alkyl oxide groups having the formula $OR_2(OH)_n(NR_3R_4)_m$, wherein n and m are numbers ranging from 0 to 10, $R_2$ is an alkyl group having from 1 to 7 carbon atoms, $R_3$ and $R_4$ are each independently hydrogen or an alkyl group such that the sum of the carbon atoms of $R_3$ and $R_4$ ranges from 1 to 7, and wherein the corresponding acrylic polymer is water-soluble;
copolymers of an acrylic polymer of formula (IX) and one or more of the following neutral monomers:
vinyl acetate;
N-vinyllactam;
maleic anhydride;
vinyl alkyl ethers of formula (V):

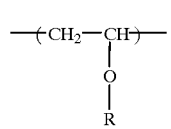

(V)

in which R is selected from the group consisting of alkyl groups containing from 1 to 7 carbon atoms;
neutral acrylic derivative of formula (VI):

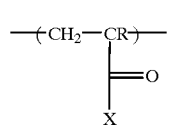

(VI)

in which R is hydrogen or a methyl group, and X is selected from the group consisting of alkyl oxide having the formula OR' where R' is an alkyl group having 1 to 7 carbon atoms; hydroxylated and/or aminated alkyl oxide having the formula $OR_1(OH)_n(NR_2R_3)_m$ where n and m are each independently numbers ranging from 0 to 10, $R_1$ is an alkyl group having 1 to 7 carbon atoms; $R_2$ and $R_3$ are each independently hydrogen or an alkyl group such that the sum of the carbon atoms of $R_2$ and $R_3$ ranges from 1 to 7; and primary, secondary or tertiary amine having the formula $NR_2R_3$ where $R_2$ and $R_3$ have the meaning indicated above.

12. The nanoemulsion according to claim 1, wherein said water soluble nonionic polymer (ii) present in said nanoemulsion is hydroxypropyl guar.

13. The nanoemulsion according to claim 1, wherein said water-soluble nonionic polymer is present in an amount ranging from 0.01 to 20% by weight relative to the total weight of the composition.

14. The nanoemulsion according to claim 1, wherein said nonionic amphiphilic lipid present in said nanoemulsion is one or more selected from the group consisting of:
(1) silicone surfactants,
(2) amphiphilic lipids which are liquid at a temperature of less than or equal to 45° C. and which are selected from the group consisting of esters of at least one polyol and of at least one fatty acid having at least one saturated or unsaturated and linear or branched $C_8$–$C_{22}$ alkyl chain,
(3) esters of fatty acid and of sugar,
(4) ethers of fatty alcohol and of sugar,
(4) surfactants which are solid at a temperature of less than or equal to 45° C. and which are selected from the group consisting of glycerol fatty esters, sorbitan fatty esters, oxyethylenated sorbitan fatty esters, ethoxylated fatty ethers, and 5 ethoxylated fatty esters, (5) block copolymers of ethylene oxide and of propylene oxide, and mixtures thereof.

15. The nanoemulsion according to claim 1, wherein said amphiphilic lipid (i) is present in an amount ranging from 0.2 to 15% by weight with respect to the total weight of the composition.

16. The nanoemulsion according to claim 1, further comprising at least one additional ionic amphiphilic lipid.

17. The nanoemulsion according to claim 16, wherein said additional ionic amphiphilic lipid is present in an amount ranging from 0.01 to 10% by weight with respect to the total weight of the composition.

18. The nanoemulsion according to claim 1, wherein said oily phase is present in an amount ranging from 2 to 40% by weight with respect to the total weight of the composition.

19. A cosmetic or dermatological composition, comprising the nanoemulsion as claimed in claim 1.

20. An ophthalmic vehicle, comprising the nanoemulsion as claimed in claim 1.

21. A pharmaceutical composition, comprising the nanoemulsion as claimed in claim 1.

22. A method for caring for, treating, or making up the skin, face, or scalp, comprising applying the nanoemulsion as claimed in claim 1 to the skin, face, or scalp.

23. A method for caring for or treating the hair, comprising applying the nanoemulsion as claimed in claim 1 to the hair.

24. A method for caring for or moisturizing the skin, mucous membranes, or scalp, comprising applying the nanoemulsion as claimed in claim 1 to the skin, mucous membranes, or scalp.

25. A method of making a composition intended for the treatment of dry skin, comprising admixing the nanoemulsion as claimed in claim 1 with said composition.

26. A method of making an ophthalmological composition, comprising admixing the nanoemulsion as claimed in claim 1 with said composition.

27. A method for preparing the nanoemulsion as claimed in claim 1, comprising:

combining said oily phase, said aqueous phase, and said amphiphilic lipid with high pressure homogenization to obtain a first nanoemulsion, and thereafter contacting said nanoemulsion with said water-soluble nonionic polymer (ii) to obtain said nanoemulsion as claimed in claim 1.

28. The nanoemulsion according to claim 1, wherein the at least one water-soluble nonionic polymer present in said nanoemulsion is selected from the group consisting of homopolymers of ethylene oxide; polyvinyl alcohols; homopolymers and copolymers of vinylpyrrolidone; homopolymers and copolymers of vinylcaprolactam; homopolymers and copolymers of polyvinyl methyl ether; neutral acrylic homopolymers and copolymers; $C_1$–$C_3$ alkyl guar; $C_1$–$C_3$ hydroxyalkyl guar; and combinations thereof.

29. The nanoemulsion according to claim 1, wherein the at least one water-soluble nonionic polymer present in said nanoemulsion is selected from the group consisting of polyvinyl alcohols; homopolymers and copolymers of vinylpyrrolidone; homopolymers and copolymers of vinylcaprolactam; homopolymers and copolymers of polyvinyl methyl ether; neutral acrylic homopolymers and copolymers; $C_1$–$C_3$ alkyl guar; $C_1$–$C_3$ hydroxyalkyl guar; and combinations thereof.

30. The nanoemulsion according to claim 1, wherein the water-soluble nonionic polymer is present in an amount sufficient to increase the viscosity of said nanoemulsion by at least a factor of 5.

31. The nanoemulsion according to claim 1, having a turbidity ranging from 70 to 300 NTU.

32. The nanoemulsion according to claim 1, having a turbidity ranging from 70 to 150 NTU.

33. The nanoemulsion according to claim 1, having a turbidity ranging from 100 to 200 NTU.

* * * * *